United States Patent
Kirenko et al.

(10) Patent No.: US 11,356,554 B2
(45) Date of Patent: Jun. 7, 2022

(54) DEVICES, SYSTEM AND METHODS FOR DETERMINING A PRIORITY LEVEL AND/OR CONVERSATION DURATION OF A CALL

(71) Applicant: KONINKLIJKE PHILIPS N.V., Eindhoven (NL)

(72) Inventors: Ihor Olehovych Kirenko, Veldhoven (NL); Chaitanya Dongre, Vaals (NL); Ronaldus Maria Aarts, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 653 days.

(21) Appl. No.: 16/071,631

(22) PCT Filed: Feb. 13, 2017

(86) PCT No.: PCT/EP2017/053094
§ 371 (c)(1),
(2) Date: Jul. 20, 2018

(87) PCT Pub. No.: WO2017/144293
PCT Pub. Date: Aug. 31, 2017

(65) Prior Publication Data
US 2021/0176357 A1    Jun. 10, 2021

(30) Foreign Application Priority Data
Feb. 25, 2016  (EP) .................... 16157260

(51) Int. Cl.
*H04W 4/16*     (2009.01)
*H04M 3/436*   (2006.01)
(Continued)

(52) U.S. Cl.
CPC ......... *H04M 3/4365* (2013.01); *A61B 5/0013* (2013.01); *A61B 5/0022* (2013.01);
(Continued)

(58) Field of Classification Search
CPC .. H04M 3/4365; A61B 5/0013; A61B 5/0022; G10L 25/63; G10L 25/66
(Continued)

(56) References Cited

U.S. PATENT DOCUMENTS 7,151,826 B2 * 12/2006 Shambaugh ............ H04M 3/51
                                                           379/265.02
8,498,403 B1 *  7/2013 Coughlan ........... H04M 3/5233
                                                           379/265.06
(Continued)

FOREIGN PATENT DOCUMENTS

EP        2765762           8/2014
JP     2002236759 A        8/2002
(Continued)

OTHER PUBLICATIONS

Verkruysse et al., "Remote plethysmographic imaging using ambient light", Optics Express, 16(26), Dec. 22, 2008, p. 21434-21445.

Primary Examiner — William J Deane, Jr.

(57) ABSTRACT

The present invention relates to device, system and method for determining a priority level and/or conversation duration of a call. An improved and adaptive device comprises a signal input (31) for obtaining an image data signal (21) of a user initiating a call, a physiological data extraction unit (32) for extracting physiological data (22) of the user from the obtained image data signal (21), a health condition determination unit (33) for determining the health condition (23) of the user based on the extracted physiological data, and a prioritization unit (34) for determining the priority level and/or conversation duration (24) of the call based on the determined health condition of the user.

12 Claims, 5 Drawing Sheets

(51) Int. Cl.
    *A61B 5/00*      (2006.01)
    *G10L 25/63*     (2013.01)
    *G10L 25/66*     (2013.01)
    *H04M 3/22*      (2006.01)
    *G16H 50/30*     (2018.01)

(52) U.S. Cl.
    CPC .............. *G10L 25/63* (2013.01); *G10L 25/66* (2013.01); *G16H 50/30* (2018.01); *H04M 3/2281* (2013.01)

(58) Field of Classification Search
    USPC .... 455/415, 414.1, 412; 379/265.01–265.14, 379/266.01–266.1, 309, 201.01, 88.01
    See application file for complete search history.

(56) References Cited

U.S. PATENT DOCUMENTS

| | | | |
|---|---|---|---|
| 8,825,786 B1* | 9/2014 | Webb, III | G16H 10/60 709/206 |
| 9,195,900 B2* | 11/2015 | Gu | G06K 9/46 |
| 9,801,544 B2 | 10/2017 | Norita | |
| 10,045,702 B2 | 8/2018 | Jeanne | |
| 2004/0062363 A1* | 4/2004 | Shambaugh | H04M 3/51 379/88.01 |
| 2005/0069852 A1* | 3/2005 | Janakiraman | H04M 1/2474 434/236 |
| 2005/0163302 A1 | 7/2005 | Mock | |
| 2006/0161457 A1* | 7/2006 | Rapaport | G16H 10/20 705/2 |
| 2006/0293921 A1* | 12/2006 | McCarthy | A61B 5/6815 705/2 |
| 2008/0037762 A1 | 2/2008 | Shaffer | |
| 2009/0105550 A1 | 4/2009 | Rothman | |
| 2010/0052915 A1* | 3/2010 | Allen | G06F 19/00 340/573.1 |
| 2011/0040191 A1* | 2/2011 | Kyle | A61B 5/015 600/473 |
| 2013/0142322 A1* | 6/2013 | Grasso | G06Q 10/06398 379/265.08 |
| 2013/0345568 A1* | 12/2013 | Mestha | A61B 5/02405 600/473 |
| 2014/0016768 A1* | 1/2014 | Turcan | H04M 3/42323 379/265.09 |
| 2014/0191863 A1 | 7/2014 | Ten | |
| 2014/0221781 A1* | 8/2014 | Schrauf | A61B 5/02055 600/301 |
| 2015/0066525 A1* | 3/2015 | Webb, III | G16H 80/00 705/2 |
| 2015/0213205 A1 | 7/2015 | Van de Sluis | |
| 2015/0379362 A1 | 12/2015 | Calmes | |
| 2016/0156779 A1* | 6/2016 | Deshmukh | G06Q 30/01 379/265.06 |
| 2017/0024704 A1* | 1/2017 | Tompkins | G06Q 10/1095 |
| 2018/0047120 A1* | 2/2018 | Mathis | G16H 10/60 |
| 2020/0077892 A1* | 3/2020 | Tran | G08B 25/016 |
| 2020/0195781 A1* | 6/2020 | Babjack | H04M 3/5233 |
| 2020/0294683 A1* | 9/2020 | Gutman | H04L 67/12 |

FOREIGN PATENT DOCUMENTS

| | | |
|---|---|---|
| JP | 2003022326 A | 1/2003 |
| JP | 2008113679 A | 5/2008 |
| JP | 2008229172 | 10/2008 |
| JP | 2011082839 A | 4/2011 |
| JP | 2015119898 A | 7/2015 |
| WO | 2007070247 | 6/2007 |
| WO | 2010052613 | 5/2010 |
| WO | 2014/064580 | 5/2014 |
| WO | 2015/044826 | 4/2015 |
| WO | 2015/055709 | 4/2015 |

\* cited by examiner

DEVICES, SYSTEM AND METHODS FOR DETERMINING A PRIORITY LEVEL AND/OR CONVERSATION DURATION OF A CALL

CROSS REFERENCE TO RELATED APPLICATIONS

This application is the U.S. National Phase application under 35 U.S.C. § 371 of International Application No. PCT/EP2017/053094, filed Feb. 13, 2017, published as WO 2017/144293 on Aug. 31, 2017, which claims the benefit of European Patent Application Number 16157260.7 filed Feb. 25, 2016. These applications are hereby incorporated by reference herein.

FIELD OF THE INVENTION

The present invention relates to devices, system and methods for determining a priority level and/or conversation duration of a call.

BACKGROUND OF THE INVENTION

There is growing evidence that home telemonitoring can be advantageous in societies with increasing prevalence of chronic diseases. Moreover, support of elderly patients at home can be provided more efficiently using telemonitoring systems. Home telemonitoring represents a patient management approach combining various information technologies for monitoring patients at distance. Regular communication of a patient with a care coordination centrum via audio/video communication tools is an important component of such approach.

The fast growing expansion of telemonitoring systems should not negatively impact the quality of the service provided to patients. Among other that means that patients should always have an opportunity to communicate with a care centrum, if needed. Such communication service can be provided by means of additional employees (nurses) available at call centrums. However, even a significant increase of the personal and technical resources at call centers, and introduction of strict scheduling of calls would not always mitigate the possibility of overloading of the care centrum with incoming calls with various priority levels. That might lead to the chance that an urgent call (e.g. related to deterioration of a health condition) would not get through fast enough. Moreover, strict static scheduling of call duration might be not always optimal for a wide range of patients, since some of them might require much more time for proper conversation than others. It also leads to high pressure situations for the remote caregiver as he is often under time pressure to conclude (hang up) on a call as he sees visually the queue of calls waiting to be answered on a screen in front of him/her. In such situations he might not be able to provide the best possible care to the customer. It may also be detrimental to the health and wellbeing of the caregiver (in many applications mentioned below a typical caregiver would be an employee of a call center or a customer representative).

US 2005/0163302 A1 discloses a customer service method for handling calls to or from a plurality of callers. Said method can include the steps of retrieving non-vocal physiological data from a caller, assigning a priority to the caller in response to retrieving non-vocal physiological data from the caller, and routing the caller based on the priority assigned to the caller. The method can further include the step of retrieving vocal physiological data from the caller and assigning the priority in response to retrieving both the non-vocal physiological data and vocal physiological data. The routing of the caller can also be based on the priority assigned to the caller and a value determined for the caller from a profile for the caller. Priority given to low and high value callers can be altered based on when and what physiological data is received.

SUMMARY OF THE INVENTION

It is an object of the present invention to provide improved and adaptive devices, system and methods for determining a priority level and/or conversation duration of a call.

In a first aspect of the present invention a device for determining a priority level and/or conversation duration of a call is presented comprising:
a signal input for obtaining an image data signal of a user initiating a call,
a physiological data extraction unit for extracting physiological data of the user from the obtained image data signal,
a health condition determination unit for determining the health condition of the user based on the extracted physiological data, and
a prioritization unit for determining the priority level and/or conversation duration of the call based on the determined health condition of the user.

In a second aspect of the present invention a device for determining a priority level and/or conversation duration of a call is presented comprising:
a health condition input for obtaining a health condition of a user, said health condition being determined from physiological data extracted from an image data signal of a user initiating a call, and
a prioritization unit for determining the priority level and/or conversation duration of the call based on the determined health condition of the user.

In a third aspect of the present invention a system for determining a priority level and/or conversation duration of a call is presented comprising:
an image data sensor, in particular a camera, for acquiring image data of a user initiating a call and for generating an image data signal, and
a device as disclosed herein for determining a priority level and/or conversation duration of the call based on the generated image data signal.

In yet further aspects of the present invention, there are provided corresponding methods, a computer program which comprises program code means for causing a computer to perform the steps of one of the methods disclosed herein when said computer program is carried out on a computer as well as a non-transitory computer-readable recording medium that stores therein a computer program product, which, when executed by a computer, a processor, or a network, causes one of the methods disclosed herein to be performed.

Preferred embodiments of the invention are defined in the dependent claims. It shall be understood that the claimed system, methods, computer program and medium have similar and/or identical preferred embodiments as the claimed device, in particular as defined in the dependent claims and as disclosed herein.

The present invention is based on the idea to determine the health condition of the user who is initiating a call, e.g. to a care centrum, based on extracted physiological data and to use the information on the health condition of the user to determine the priority level and/or conversation duration of the call. In this way, an adaptive prioritization and scheduling of a call time and a call duration from e.g. patients (i.e. subjects of a telemonitoring system or users of the proposed device or method) to a care centrum can be made based on measured vital signs and other physiological parameters of a patient just before and/or during the conversation, e.g. during a waiting time after initiating the call until the call is received. An automated definition of the priority level of unscheduled calls of patients of a telemonitoring system to a call care centrum and of the duration of scheduled conversations can thus be made.

In this context, "priority level" shall be understood as any information related to the priority with which a call shall be treated, i.e. which may be used for prioritization of the call. This may particularly include a priority relative to other calls from other users, but may also include priority information indicating e.g. the urgency of the call (such as "low", "medium" or "high") without any relation to the calls of other users.

Furthermore, also trends in user wellbeing, e.g. physical and mental wellbeing might of a patient, may be useful in prioritizing, e.g. data measured at different times of the day (e.g. at night owing to high fall risk), specific days of the week (e.g. the day after a visit by grandchildren the elderly might feel more lonely than usual), or in different months/seasons (e.g. in winter symptoms of depression or lack of physical activity).

The proposed device may be part of the device used by the user for initiating the call, such as a smartphone or regular telephone, or may be part of the receiving device, e.g. a call center or a care center of a hospital. Further, in other embodiments some or all of the steps of the proposed method are carried out on the side of the caller, while the other steps are carried out on the side of the receiver (also called recipient). For instance, the user's health condition may be determined on the side of the user and is then, when the call is initiated, transmitted to the receiver, where the priority level and/or conversation duration of the call is determined based on the received health condition of the user. Hereby, a ranking can then be performed among several simultaneously calling users by comparing their respective priority levels and/or conversation durations.

Hence, the device proposed according to the first aspect of the present invention is generally arranged on the side of the caller, while the device proposed according to the second aspect of the present invention may generally be arranged either on the side of the caller or (preferably) on the side of the receiver, for instance in a switchboard or call center.

In an embodiment said physiological data extraction unit is configured to derive a photoplethysmography (PPG) signal from the obtained image data signal and to extract one or more vital signs as physiological data from said PPG signal. The technique for deriving PPG signals from images, particular of a skin area of a person, and for deriving vital signs from such PPG signals is commonly known, e.g. from Verkruysse et al., "Remote plethysmographic imaging using ambient light", Optics Express, 16(26), 22 Dec. 2008, pp. 21434-21445 and many other publications directed to remote PPG. Using PPG technology, vital signs (e.g. the heart rate (HR), the respiration rate (RR) or the arterial blood oxygen saturation) can be measured, which are revealed by minute light absorption changes in the skin caused by the pulsating blood volume, i.e. by periodic color changes of the human skin induced by the blood volume pulse. These vital signs can thus be acquired without any additional contact sensor and can then be used in the determination of the user's health condition.

The device may further comprise a stress estimation unit for estimating the stress level and/or emotional state of the user from the obtained image data signal and/or the extracted physiological data. The estimated stress level and/or emotional state of the user can then additionally be used in the determination of the priority level and/or conversation duration of the call to further improve the correctness of said determination.

In an embodiment said signal input is configured to obtain an audio data signal of the user and said stress estimation unit is configured to additionally use the obtained audio data signal in the estimation of the stress level and/or emotional state of the user. The audio data signal can be easily obtained by the device used for initiating the call, e.g. the microphone of the used telephone. The audio signal further improves the correct estimation of the stress level and/or emotional state of the user.

In another embodiment said stress estimation unit is configured to perform a face detection and analysis by use of the obtained image data signal and/or a voice analysis by use of the obtained audio data signal and to use the result of said analysis in the estimation of the stress level and/or emotional state of the user. This also contributed to a further improvement of the correct estimation.

In another embodiment said signal input unit is configured to obtain one or more sensor signals from one or more wearable sensors and said health condition determination unit is configured to additionally use the obtained one or more sensor signals in the determination of the health condition of the user. Such wearable sensors may e.g. include one or more of a respiration sensor, a pulse sensor, a SpO2 sensor, an EDA (electrical dermal activity) sensor, an accelerometer, a skin conductivity sensor, etc. The signal acquire by such sensors may be coupled to the device in a wired or wireless manner, using e.g. Bluetooth, WiFi, Zigbee, etc.

Said prioritization unit may be configured to determine routing information indicating to which service or person or to which kind of service or person the call shall be routed. Hence, the calling user can thus be quickly and directly connected to the right person or service, e.g. a specialist who is specialized for the user's problem.

The device may further be configured to determine the priority level and/or conversation duration of the call just before, while or just after the call is initiated, in particular during a holding time between initiation of the call by the user and acceptance of the call by the receiver of the call, i.e. the person to whom the call is directed. This avoids losing any potentially valuable time for performing computations during extra time.

Still further, in an embodiment said prioritization unit is configured to compare the determined health condition of the user with a previously determined health condition of the user and/or with a health condition baseline of the user and/or with a general health condition threshold and for using the result of the comparison in the determination of the priority level and/or conversation duration of the call. This further improves the correct determination of the priority level and/or conversation duration by taking the patient history into account and helps to better and quickly recognize a real degradation of the user's health condition.

The device may further comprise an image processing unit for deriving health-related information from the obtained image data signal by detecting movement of one or more body parts and/or gestures and/or mimic and/or posture, wherein said health condition determination unit is configured to additionally use said health-related information in the determination of the health condition of the user. This also improves the reliability of the determination of the user's health condition.

The proposed device according to the second aspect of the present invention, particularly for use on the receiver's side, may further comprise a call handling unit (e.g. a switchboard) for handling the call according to the priority and/or conversation duration determined for the call.

According to a further embodiment said call handling unit may be configured to compare the priority level determined for the actual call with the priority level determined for other calls received earlier and still waiting for being transferred to the right service or person and/or received later while the actual call is still waiting for being transferred to the right service or person, and to use the result of the comparison in the handling of the actual call. Thus, the priority levels of various callers desiring the same service may be compared to determine the sequence, in which the callers are forwarded to the desired service.

The proposed system may, in addition to the an image data sensor and the proposed device, further comprise an audio data sensor, in particular a microphone, for acquiring audio data of the user and for generating an audio data signal and/or one or more wearable sensors for acquiring one or more sensor signals, which additional signals may also be provided to the device for use in the processing as explained above.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
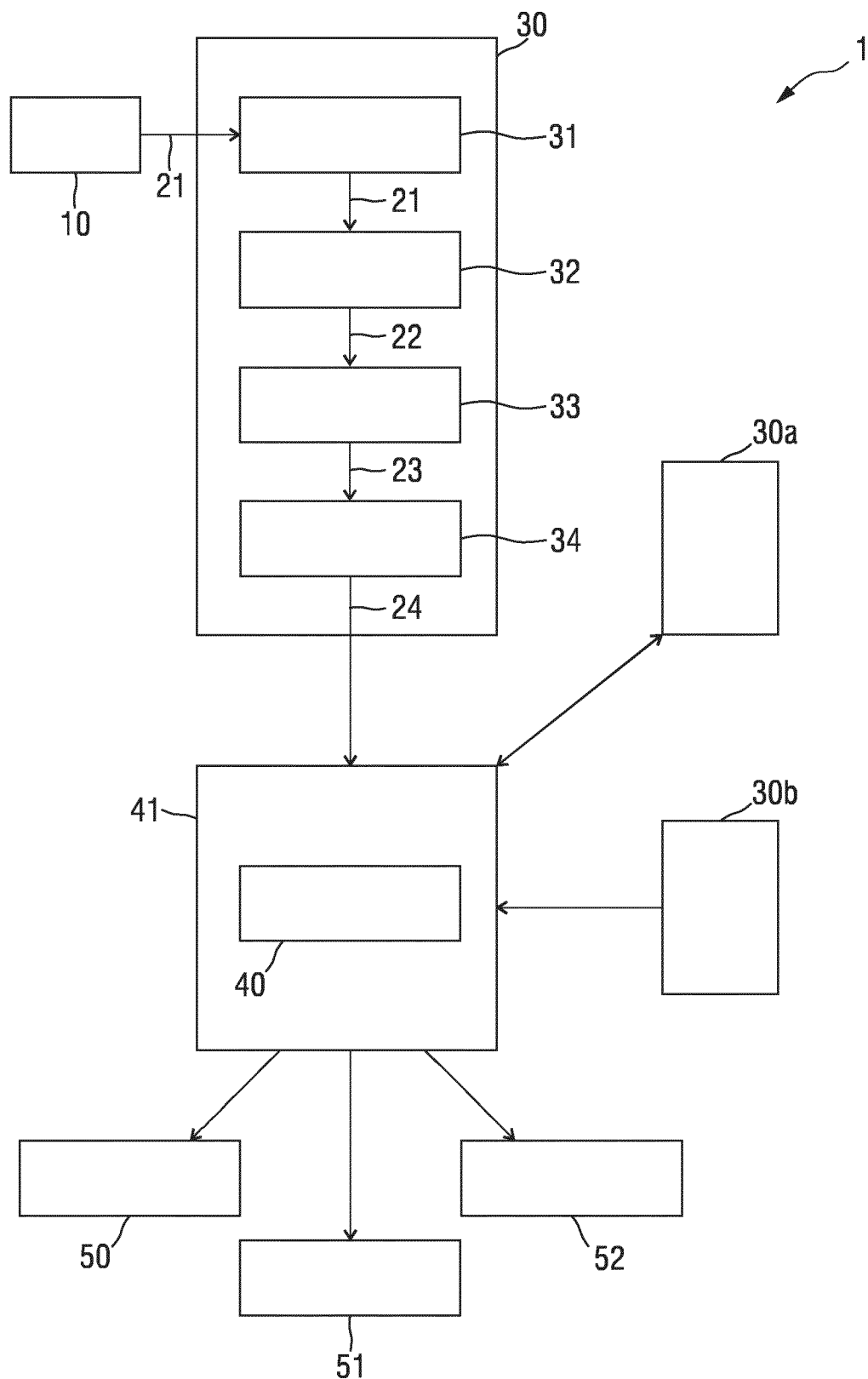
FIG. 1 shows a schematic diagram of a first embodiment of a system and a device according to the present invention.

FIG. 1 shows a schematic diagram of a first embodiment of a system 1 and a device 30 according to the present invention. The system 1 comprises an image data sensor 10, such as a camera, for acquiring image data of a user, e.g. a patient at home, initiating a call and for generating an image data signal 21. The image data signal 21 is provided to a device 30 for determining a priority level and/or conversation duration, represented by information signal 24, of the call initiated by the user based on the generated image data signal 21, as will be explained in more detail below. The priority level and/or conversation duration, represented by information signal 24, determined for the call is provided to a call handling unit 40 for handling the call according to the determined priority level and/or conversation duration.

In an exemplary use scenario, a patient (i.e. the caller) at home seeks to contact a particular service or person among a plurality of services or persons 50, 51, 52, e.g. a specialist in a hospital or care center, via telephone. External calls to the hospital or care center, including calls from various users having the same or similar device 30, 30a, 30b, are handled by a switchboard or call center 41 (including the call handling unit 40) within the hospital or care center or authorized by the hospital or care center. As long as only a single user seeks contact to a particular service or person, the call can be received immediately. However, if several users seek contact to the same service or person, a prioritization has to be made which caller is connected to the service or person first. This prioritization may be made by the call handling unit 40 based on information received from the devices 30, 30a, 30b about the priority level of the respective caller. Furthermore, information on the conversation duration may be taken into account in said prioritization, e.g. to handle short conversation of a number of callers first, before a long conversation with another caller is made.

The imaging unit 10 may e.g. include a camera including a suitable photosensor for (remotely and unobtrusively) capturing image frames of the, in particular for acquiring a sequence of image frames of the user over time. Such cameras are part of many user devices, such as smartphones, tablets, laptops, or may be provided as external entity (e.g. as webcam) coupled to a user device. Hence, e.g. the camera of a smartphone used for making the call may be used as imaging unit 10.

In an embodiment, the image frames captured by the imaging unit 10 may particularly correspond to a video sequence captured by means of an analog or digital photosensor, e.g. in a (digital) camera. Such a camera usually includes a photosensor, such as a CMOS or CCD sensor, which may also operate in a specific spectral range (visible, IR) or provide information for different spectral ranges. The camera may provide an analog or digital signal. The image frames include a plurality of image pixels having associated pixel values. Particularly, the image frames include pixels representing light intensity values captured with different photosensitive elements of a photosensor. These photosensitive elements may be sensitive in a specific spectral range (i.e. representing a specific color/weighted sum of wavelengths). Preferably, the image frames include at least some image pixels being representative of a skin portion of the subject so that photoplethysmography (PPG) signals can be derived from said image frames. Thereby, an image pixel may correspond to one photosensitive element of a photodetector and its (analog or digital) output or may be determined based on a combination (e.g. through binning, or spatial filtering) of a plurality of the photosensitive elements.

The device 30 may be implemented in soft- and/or hardware, e.g. by an application software ("app") configured to run on a processor of e.g. the smartphone used by the user for making the call. The device 30 includes a signal input 31, e.g. a data interface coupled with the camera of the smartphone or a wireless interface (e.g. Bluetooth or WiFi) for receiving the image data signal 21 from an external camera, for obtaining (i.e. receiving or retrieving, e.g. downloading) the image data signal 21.

The device 30 further comprises a physiological data extraction unit 32 for extracting physiological data 22 of the user from the obtained image data signal 21. This may be done by deriving PPG signals from a sequence of image frames and by deriving vital signs from said PPG signals, such as the heart rate, the respiration rate, SpO2, etc.

The device 30 further comprises a health condition determination unit 33 for determining the health condition 23 of the user based on the extracted physiological data. This may be done by use of known algorithms for determining the health condition (e.g. a health score) from vital signs, as e.g. described in US 2009/0105550 A1 or WO 2015/044826 A1. For instance, one way is to determine the heart rate. If the heart rate deviates between certain limits an effect on the health condition might be given. Furthermore, health condition based on vital signs can be defined using an early warning score system as generally known and e.g. accepted by healthcare institutions. In an embodiment the user's health record (health history) may be taken into account, e.g. to determine the trend of his health condition and to see if (and, optionally, to which degree) his health condition has improved or deteriorated.

The device 30 further comprises a prioritization unit 34 for determining the priority level and/or conversation duration 24 of the call based on the determined health condition 23 of the user. Generally, the priority level is set higher if the health condition is bad and is set lower if the health condition is good. In a more sophisticated embodiment the user's trend of the health condition is taken into account (and, optionally, previous settings of the priority level). Hence, the user's relative change of the health condition may be used to set the priority level. For instance, the priority level can be set using an approach similar to an early warning score system.

The conversation duration is generally set longer if the health condition is bad and is set shorter if the health condition is good. In a more sophisticated embodiment the user's trend of the health condition is taken into account (and, optionally, previous settings of the conversation duration). Hence, the user's relative change of the health condition may also be used to set the conversation duration.

In an embodiment the prioritization unit 34 may further determine routing information indicating to which service or person 50, 51, 52 or to which kind of service or person a call from a particular user shall be routed. For instance, a profile of the service or person to which the call shall be routed may be recommended, which recommendation may be used by the call handling unit 40. For determining the routing information the health condition and/or the extracted physiological data may be used. For instance, if a separate vital sign, such as the heart rate, or a combination of several signs shows strong abnormalities and the health condition is bad, the call may be routed to an emergency service or a heart specialist.

Generally, the priority level and/or conversation duration (and, optionally, the routing information) of the call is determined just before, while or just after the call is initiated, in particular during a holding time between initiation of the call by the user and acceptance of the call by the receiver, although it is generally possible that this information is determined continuously, or at least at time when current image data of the user are available.

The prioritization unit 34 may also be configured to compare the determined health condition of the user with a previously determined health condition of the user and/or with a health condition baseline of the user and/or with a general health condition threshold and for using the result of the comparison in the determination of the priority level and/or conversation duration 24 of the call. The previously determined health condition may e.g. be stored in the device or may be retrieved from a health record, e.g. a database of the care center or hospital or a personal database of the user.

Figure 2:
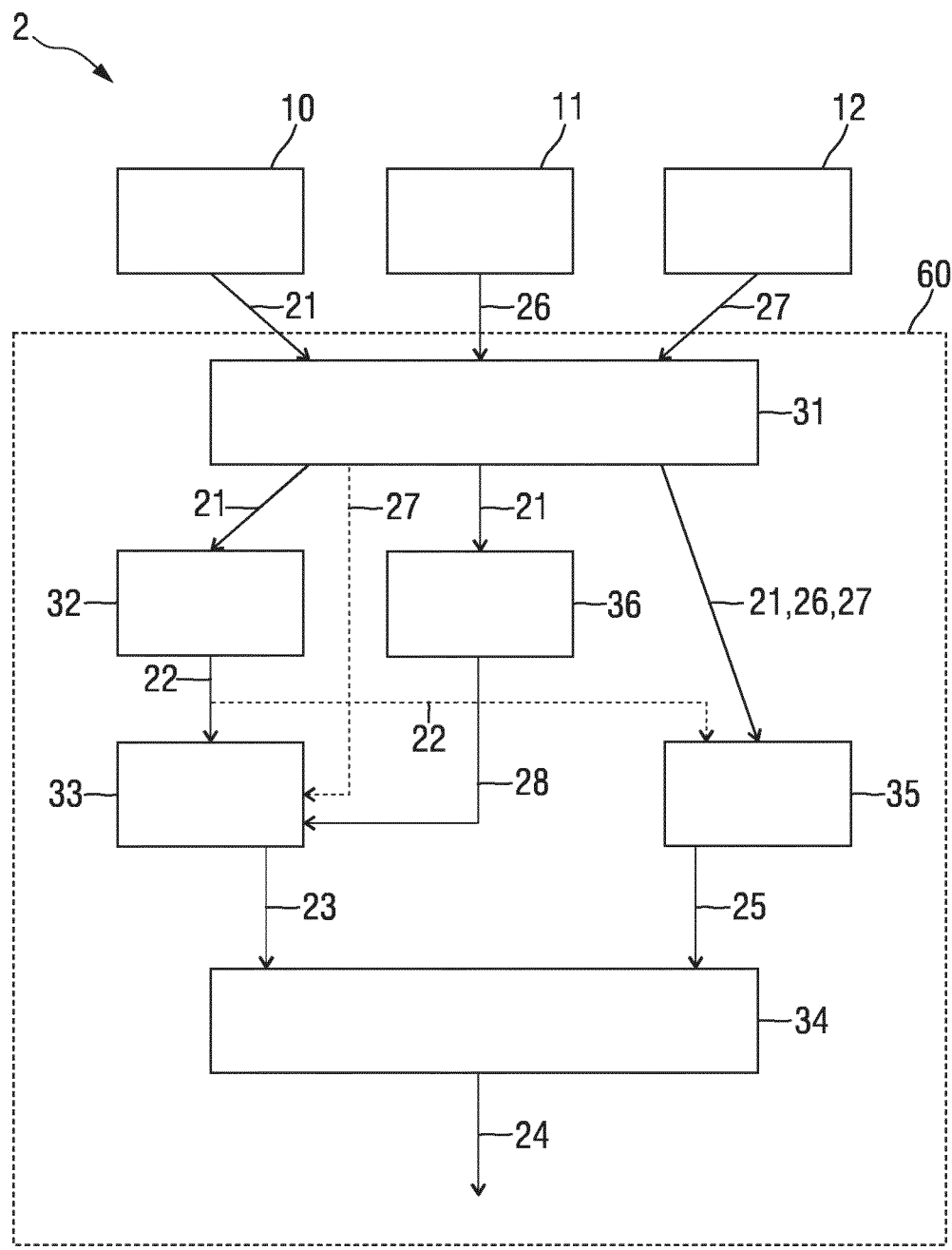
FIG. 2 shows a schematic diagram of a second embodiment of a system and a device according to the present invention.

FIG. 2 shows a schematic diagram of a second embodiment of a system 2 and a device 60 according to the present invention. In this embodiment the system further comprising one or more additional sensors for providing additional information to the device 60. These additional sensors may include an audio data sensor 11, e.g. a microphone (which may be the microphone of the smartphone used for making the call), for acquiring audio data of the user and for generating an audio data signal 26 provided to the signal input 31. These additional sensors may further include one or more wearable sensors 12 for acquiring one or more sensor signals 27. These wearable sensors 12 may include a heart rate sensor for providing a heart rate signal, a respiration sensor for providing respiration information (e.g. respiration rate, respiration depth, inhalation duration, exhalation duration, etc.), an SpO2 sensor for providing an SpO2 signal, an accelerometer for providing a motion signal, etc. Wearable sensors may thus provide the information about vital signs measured during a long period of time before the call. This information can be used as a baseline to estimate the difference between vital signs measured immediately before the call (or during the call) and the long term statistic of vital signs.

The device 60 may further comprise a stress estimation unit 35 for estimating the stress level and/or emotional state 25 of the user. The stress level and/or emotional state 25 may generally be estimated from the obtained image data signal 21 and/or the extracted physiological data 22. In addition, the obtained audio data signal 26 and/or one or more of the sensor signals 27 may be used for this purpose.

Generally, the estimation of the stress level and/or the emotional state of a person from physiological data, e.g. from vital signs, is known, e.g. from U.S. Pat. No. 8,684,924 B2 or WO 2014/064580 A1. For instance, known methods for measuring stress is looking at the heart rate variability, electrodermal activity (EDA, also known as Galvanic Skin Response (GSR)).

In an embodiment the stress estimation unit 35 performs a face detection and analysis of the obtained image data signal 21 and/or a voice analysis of the obtained audio data signal 26 and uses the result of said analysis in the estimation of the stress level and/or emotional state 25 of the user.

The one or more sensor signals 27 may additionally be used by the health condition determination unit 33 in the determination of the health condition of the user.

Additionally, an image processing unit 36 may be provided for deriving health-related information 28 from the obtained image data signal 21. The image processing unit may use commonly known tools to detect movement of one or more body parts, gestures, mimic, posture, etc., which may then additionally be used by the health condition determination unit 33 in the determination of the health condition 23 of the user.

Figure 3:
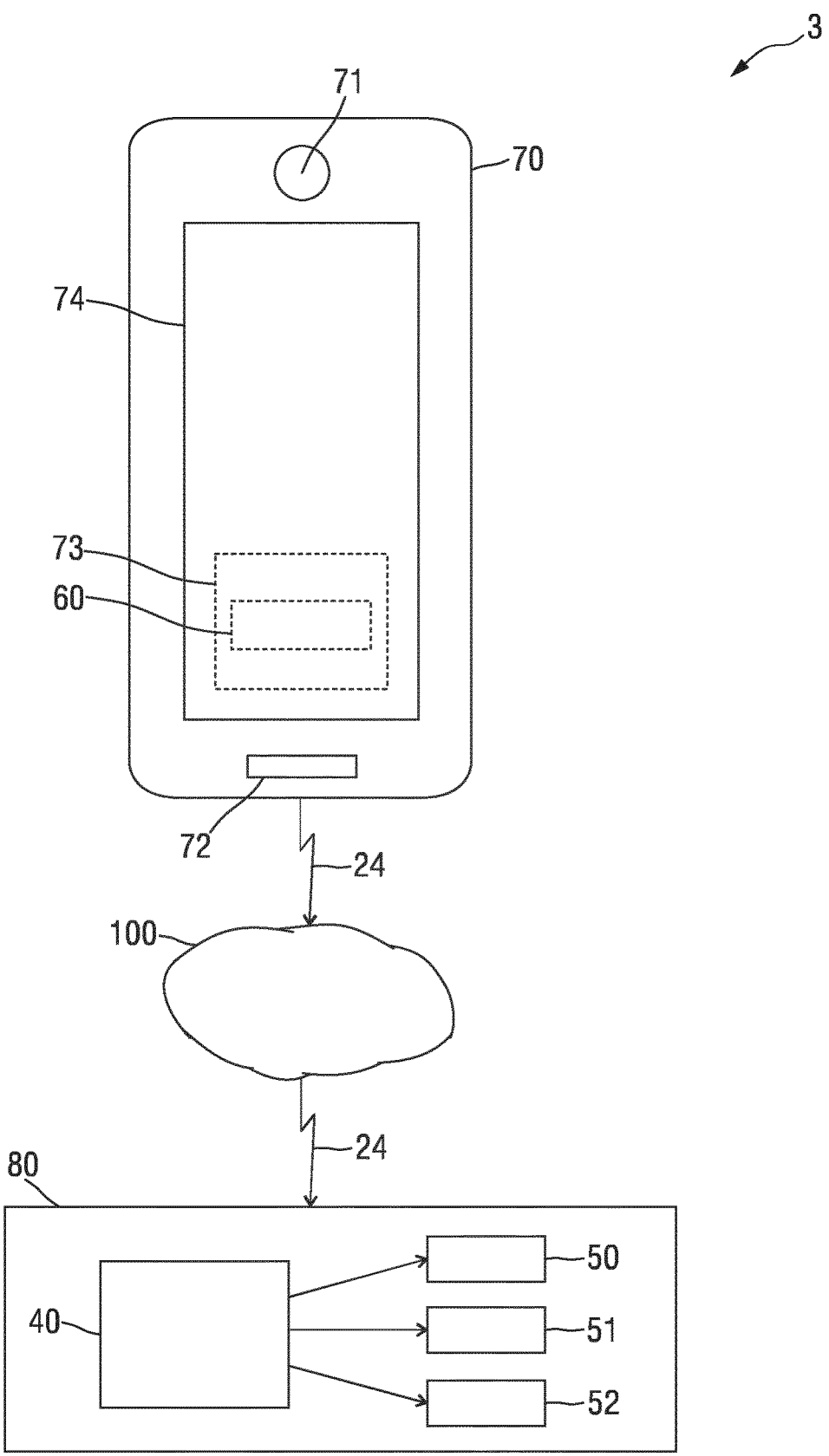
FIG. 3 shows a schematic diagram of a third embodiment of a system according to the present invention.

In a practical scenario the system might use the communication device itself for acquisition of vital body signs and physiological parameters, which avoids the need for extra (contact) sensors. Such a scenario is illustrated in FIG. 3 showing a schematic diagram of a third embodiment of a system 3 including a device 60 (or 30) according to the present invention. For instance, a camera 71 of a smartphone 70 can be used to measure pulse and respiratory rates for estimating the health condition. The microphone 72 of the smartphone 70 can be used to acquire an audio signal used additionally in estimating the health condition and/or the user's emotions and stress level based on a voice analysis. For instance, an EDA of a patient may be used based on analysis of the patient's face image. Moreover, the system can make use of other sensors of a personal device (e.g. accelerometer of a smartphone to detect hands tremor), or wearable sensors for measuring vital signs continuously.

The device 60 may be implemented in software running on the smartphone's processor 73. A display (e.g. touchpad) 74 is provided as user interface for initiating the call, depicting information (e.g. the user's health condition) or even for asking questions to the user about his health condition so that additional information may be obtained if needed to further improved the determination of the health condition.

The determined priority level and/or conversation duration 24 is transmitted, via a network 100 (e.g. the Internet, a communications network such as UMTS or LTE) to a call center or hospital 80 including the call handling unit 40, from where the various calls are routed to the respective receivers 50, 51, 52.

Thus, according to the present invention, based on the current health status, evaluated based on camera-based measured vital signals, and optionally emotional state/stress level, the system can determine the relative importance of a contact of a patient with a care center, provide suggestions regarding the duration of the call, and a recommended profile of a person at the care centrum. In case the proposed system detects signs of deterioration of a health condition of a patient compared to previous session, or unusual emotional level, the call may receive a higher priority level.

Figure 4:
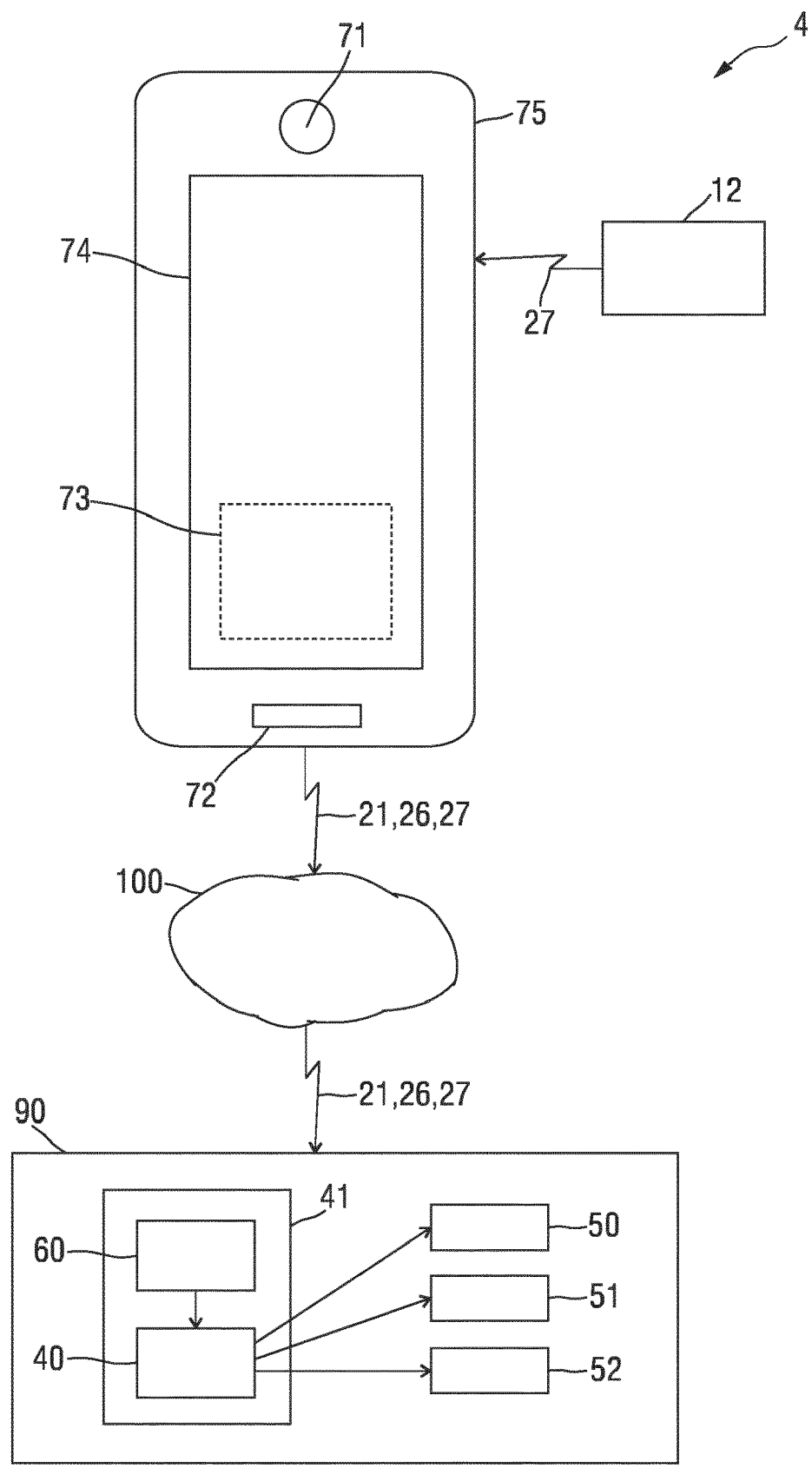
FIG. 4 shows a schematic diagram of a fourth embodiment of a system according to the present invention.

FIG. 4 shows a schematic diagram of a fourth embodiment of a system 4 according to the present invention. In this embodiment the device 60 (or 30) is arranged at the receiving entity, e.g. as part of a switchboard or call center 41 within e.g. a hospital 90. In this case, the user device 75 may be a conventional smartphone, which merely collects image data and, optionally, audio data and/or other sensor signal and transmits them via the network to the switchboard or call center 41. Here, these data are then processed by the device 60 (or 30) in the way as explained above. The priority level, conversation duration and/or routing information for many or all calling users is thus generated on the side of the receiver, so that no large modifications of the user devices are required.

Figure 5:
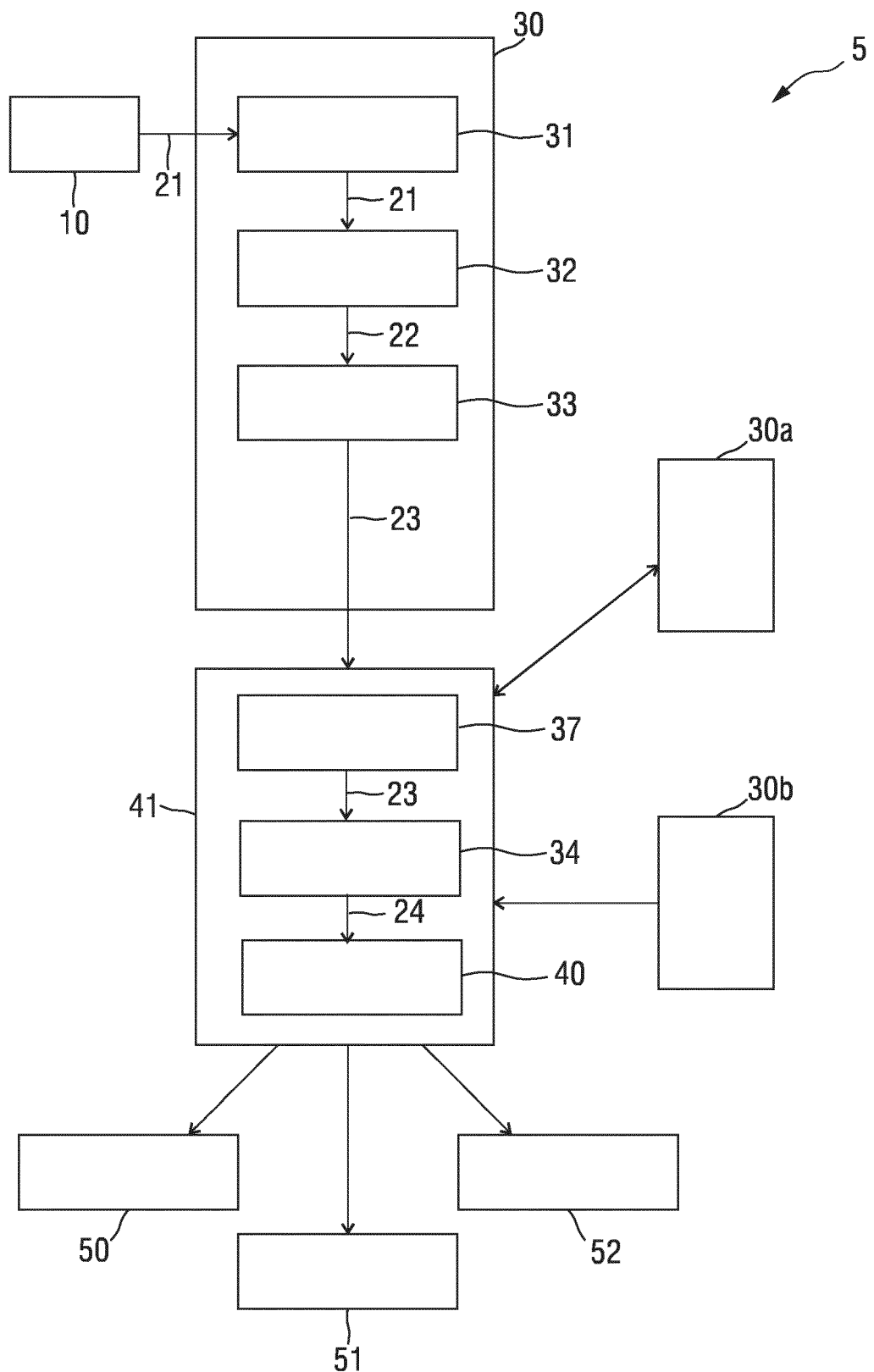
FIG. 5 shows a schematic diagram of a fifth embodiment of a system according to the present invention.

In still another embodiment the processing of the acquired data and sensor signals is partly done on the side of the caller and partly on the side of the receiver. This is illustrated in the embodiment of the system 5 shown in FIG. 5. In this embodiment the device 30 comprises only elements 31-33. For instance, the health condition 23 (and, optionally, the stress level and emotional state) may be acquired during the initialization of the call in the user device. The determined health condition 23 (and, optionally, the stress level and emotional state) are then sent to the switchboard or call center 41 for further processing, i.e. for determining the priority level, conversation duration and/or routing information. Hence, the switchboard or call center 41 comprises a health condition input 37 for obtaining the health condition 23 (and, optionally, the stress level and emotional state) of a user and the prioritization unit 34 for determining the priority level and/or conversation duration 24 of the call based on the determined health condition 23 of the user. The priority level and/or conversation duration 24 are then further processed by the call handling unit 40.

The inputs received in such an embodiment at the switchboard or call center 41 may then be compared with the values acquired during previous sessions (or a baseline for this patient). The obtained differences between the currently measured values and the previous values (or baselines) of patients may be ranked at the call handling unit 40. Thus, if two patients try to reach the call center, the incoming call from a patient with the largest difference (largest deterioration of health condition and emotional state) may receive the highest priority level. Moreover, the calls from patients with the differences above a certain level may automatically be routed to a doctor, while the rest of the calls may be handled by assistants or nurses.

In another embodiment, the system may continue monitoring of health condition and/or emotional state/stress level of a patient during communication with a receiver to advise the receiver (e.g. a care giver) on the duration and type of the conversation.

Another embodiment may include building a stack of specific vital signs and/or other video/audio data during that call, which may be updated each call. Analytics on these data may adapt the "honesty" level of the prioritization to make it more and more accurate after each call made by that user. The legacy "honesty" levels of different calls may then act as a weighing factor for them in their interaction with other such calls at any given moment to determine the final priority level. The same stack may also be used to give trend input to the prioritization algorithm so that it is taken into account how the user's health performed during the last call (e.g. yesterday), one week ago, one month ago, one year ago, specific times of the day, etc. to put the "urgency" into context.

Further, tremors in the face and limbs and asymmetries in the face (e.g. due to a stroke) may be measured or determined and may then be used to decide whether a change is above or below a threshold. This might be prior to the video call, while the patient just sits as during a normal video call, and the system might change this prioritization schedule as with a triage system. An additional benefit is that the patient already can practice with the system and gets some feedback of his health status.

In yet another embodiment the length of a call may be tracked. If this is decreasing, this is a sign that the patient feels bad, while the remote caregiver may like the short call because being very busy. However, knowing that there is a trend of decreasing chat time the caregiver may be prompted to spend longer time rather than shorter.

In yet another embodiment the remote caregiver can ask the patient to have an earlier call than originally scheduled because of own observation or alerts from the system. Further, the patient may ask for a reschedule because of various reasons e.g. the patient gets visitors, planned to do some shopping, etc.

In preferred embodiments, vital signs of a caller are used for both health condition estimation (and therefore, further decision on further steps of a care giver), and for prioritization of a call. In other words, one of the main purposes of setting a communication between a care giver and a patient is to diagnose the current state of the patient based on vital signs. The vital signs first are thus collected first and a pre-diagnosis of a health condition of a patient is made before or while the connection is installed, so that a care giver (and the communication system) knows how important the communication would be and what actions should be taken.

In one embodiment the priority level of a user to get a two-way communication audio/video call may be determined by receiving at least one physiological parameter indicative of the user's medical condition, receiving ranking information of other users during a waiting time of said two-way communication call, determining the user's place within the received ranking information based on the received at least one physiological parameter, and ranking the user's priority level on the determined user's place.

In summary, the proposed device, system and method thus provide for an adaptive scheduling of calls from patients (in general users) to a call center (in general to a receiving entity), which includes prioritization of the incoming call and/or adaptive definition of its duration. Similarly to the prioritization of the call, the call from a patient with the largest deterioration of a health condition and an emotional state may be scheduled to have a longer duration.

The proposed handling of calls improves the user experience of telemonitoring healthcare systems and mitigate the risks of non-optimal scheduling of conversation between remote patients and remote care center.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A communication device for making a call and for determining a priority level and/or conversation duration of the call, said device comprising:
    an image data sensor for acquiring image data of a user initiating a call and for generating an image data signal,
    a signal input for obtaining the image data signal of the user initiating the call,
    a physiological data extraction unit for extracting physiological data of the user from the obtained image data signal,
    a health condition determination unit for determining the health condition of the user based on the extracted physiological data, and
    a prioritization unit for determining the priority level and/or conversation duration of the call based on the determined health condition of the user,
    wherein said prioritization unit is configured to determine, without manual input from the user, routing information indicating to which healthcare service or healthcare professional the call shall be routed, and
    wherein said prioritization unit generates an adaptive scheduling dispensation based on the health condition of the user, and
    wherein a duration of the adaptive scheduling dispensation is inversely proportional to the health condition of the user.

2. The communication device as claimed in claim 1, wherein said physiological data extraction unit is configured to derive a photo-plethysmography, PPG, signal from the obtained image data signal and to extract one or more vital signs as physiological data from said PPG signal.

3. The communication device as claimed in claim 1, further comprising a stress estimation unit for estimating the stress level and/or emotional state of the user from the obtained image data signal and/or the extracted physiological data.

4. The communication device as claimed in claim 3, wherein said signal input is configured to obtain an audio data signal of the user and wherein said stress estimation unit is configured to additionally use the obtained audio data signal in the estimation of the stress level and/or emotional state of the user.

5. The communication device as claimed in claim 3, wherein said stress estimation unit is configured to perform a face detection and analysis by use of the obtained image data signal and/or a voice analysis by use of the obtained audio data signal and to use the result of said analysis in the estimation of the stress level and/or emotional state of the user.

6. The communication device as claimed in claim 1, wherein said signal input unit is configured to obtain one or more sensor signals from one or more wearable sensors and wherein said health condition determination unit is configured to additionally use the obtained one or more sensor signals in the determination of the health condition of the user.

7. The communication device as claimed in claim 1, wherein the device is configured to determine the priority level and/or conversation duration of the call just before, while or just after the call is initiated, in particular during a holding time between initiation of the call by the user and acceptance of the call by the receiver of the call.

8. The communication device as claimed in claim 1, wherein said prioritization unit is configured to compare the determined health condition of the user with a previously determined health condition of the user and/or with a health condition baseline of the user and/or with a general health condition threshold and for using the result of the comparison in the determination of the priority level and/or conversation duration of the call.

9. The communication device as claimed in claim 1, further comprising an image processing unit for deriving health-related information from the obtained image data signal by detecting movement of one or more body parts and/or gestures and/or mimic and/or posture and wherein said health condition determination unit is configured to additionally use said health-related information in the determination of the health condition of the user.

10. The communication device as claimed in claim 1, wherein the image data sensor is a camera.

11. The communication device as claimed in claim 10, further comprising an audio data sensor, in particular a microphone, for acquiring audio data of the user and for generating an audio data signal and/or one or more wearable sensors for acquiring one or more sensor signals.

12. A method for making a call and for determining a priority level and/or conversation duration of the call, said method comprising:
    acquiring image data of a user initiating a call and for generating an image data signal,
    obtaining the image data signal of the user initiating a call,
    extracting physiological data of the user from the obtained image data signal,
    determining the health condition of the user based on the extracted physiological data, determining the priority level and/or conversation duration of the call based on the determined health condition of the user, and determining, without manual input from the user, routing information indicating to which healthcare service or healthcare professional the call shall be routed, and generating an adaptive scheduling dispensation based on the health condition of the user, and a duration of the adaptive scheduling dispensation is inversely proportional to the health condition of the user.

\* \* \* \* \*